(12) United States Patent
Trinquet et al.

(10) Patent No.: US 7,998,694 B2
(45) Date of Patent: Aug. 16, 2011

(54) METHOD OF REVEALING A BIOLOGICAL PROCESS USING A FRET MEASUREMENT

(75) Inventors: Eric Trinquet, Pont Saint Esprit (FR); Hervé Ansanay, Tavel (FR); Gérard Mathis, Bagnols sur Ceze (FR)

(73) Assignee: CIS BIO International, Saclay (FR)

( * ) Notice: Subject to any disclaimer, the term of this patent is extended or adjusted under 35 U.S.C. 154(b) by 88 days.

(21) Appl. No.: 12/065,210

(22) PCT Filed: Aug. 29, 2006

(86) PCT No.: PCT/FR2006/050821
§ 371 (c)(1),
(2), (4) Date: Aug. 25, 2008

(87) PCT Pub. No.: WO2007/026099
PCT Pub. Date: Mar. 8, 2007

(65) Prior Publication Data
US 2009/0220988 A1    Sep. 3, 2009

(30) Foreign Application Priority Data
Aug. 30, 2005    (FR) .................................... 05 08857

(51) Int. Cl.
*G01N 33/567*    (2006.01)
(52) U.S. Cl. ........ 435/7.21; 435/7.2; 435/968; 436/519; 436/172; 530/391.3; 530/391.5
(58) Field of Classification Search .................... None
See application file for complete search history.

(56) References Cited

U.S. PATENT DOCUMENTS
4,637,988 A    1/1987    Hinshaw et al.
4,670,572 A    6/1987    Hinshaw et al.
4,761,481 A    8/1988    Hale et al.
4,794,191 A    12/1988    Hinshaw et al.
4,801,722 A    1/1989    Hinshaw et al.
(Continued)

FOREIGN PATENT DOCUMENTS
EP    0 180 492 A1    5/1986
(Continued)

OTHER PUBLICATIONS

Bazin et al. Time resolved amplification of cryptate emission: a versatile technology to trace biomolecular interactions, Reviews in Molecular Biotechnology (2002) 82:233-250.*

(Continued)

*Primary Examiner* — Nelson Yang
(74) *Attorney, Agent, or Firm* — Millen, White, Zelano, Branigan, P.C.

(57) ABSTRACT

The present invention relates to a method of revealing a biological process using a FRET measurement, which comprises the following steps:
  incorporating, into a measurement medium containing a lipid membrane, a biological entity X coupled with a first member of a pair of FRET partners and a second biological entity Y coupled with the second member of the pair of FRET partners, the energy-donating member of the pair of FRET partners having a long lifetime and the members of said pair of FRET partners being located on either side of the lipid membrane;
  exciting the measurement medium at the excitation wavelength of the energy-donating member; and
  measuring the FRET signal or the variations in said signal emitted in said culture medium.

23 Claims, 3 Drawing Sheets

HA-GB1+FLAG-GB2:

HA-GB1+FLAG-GB2-YFP:

U.S. PATENT DOCUMENTS

| | | | |
|---|---|---|---|
| 4,837,169 A | 6/1989 | Toner | |
| 4,859,777 A | 8/1989 | Toner | |
| 4,927,923 A | 5/1990 | Mathis et al. | |
| 5,032,677 A | 7/1991 | Hale et al. | |
| 5,055,578 A | 10/1991 | Hale et al. | |
| 5,106,957 A | 4/1992 | Hale et al. | |
| 5,116,989 A | 5/1992 | Hale et al. | |
| 5,202,423 A | 4/1993 | Kankare et al. | |
| 5,316,909 A | 5/1994 | Xu | |
| 5,324,825 A | 6/1994 | Kankare et al. | |
| 5,457,184 A | 10/1995 | Lehn et al. | |
| 5,661,035 A | 8/1997 | Tsien et al. | |
| 6,613,531 B2 * | 9/2003 | Burgess et al. | 435/7.1 |
| 7,202,349 B2 * | 4/2007 | Davis et al. | 530/402 |

FOREIGN PATENT DOCUMENTS

| | | |
|---|---|---|
| WO | WO 90/00550 A1 | 1/1990 |
| WO | WO 93/05049 A1 | 3/1993 |
| WO | WO 01/96877 A2 | 12/2001 |
| WO | WO 02/083937 A2 | 10/2002 |

OTHER PUBLICATIONS

Majoul et al. Fluorescence resonance energy transfer analysis of protein-protein interactions in single living cells by multifocal multiphoton microscopy, Reviews in Molecular Biotechnology (2002) 82:267-277.*

A. Soragna et al. "Functionally Independent Subunits in the Oligomeric Structure of the GABA Cotransporter rGAT1", Cell. Mol. Life Sci., vol. 62 (2005) pp. 2877-2885.

D. Maurel et al. "Cell Surface Detection of Membrane Protein Interaction with Homogeneous Time-Resolved Fluorescence Resonance Energy Transfer Technology", Analytical Biochemistry, vol. 329 (2004) pp. 253-262.

B. Shivers et al. "Two Novel $GABA_A$ Receptor Subunits Exist in Distinct Neuronal Subpopulations", Neuron, vol. 3 (Sep. 1989) pp. 327-337.

E. Guignet et al. "Reversible Site-Selective Labeling of Membrane Proteins in Live Cells", Letters, vol. 22, No. 4 (Apr. 2004) pp. 440-444.

G. Turcatti et al. "Probing the Structure and Function of the Tachykinin Neurokinin-2 Receptor Through Biosynthetic Incorporation of Fluorescent Amino Acids At Specific Sites", The Journal of Biological Chemistry, vol. 271, No. 33 (Aug. 1996) pp. 19991-19998.

J. Gonzalez et al., "Improved Indicators of Cell Membrane Potential That Use Fluorescence Resonance Energy Transfer", Chemistry & Biology, vol. 4 (Apr. 1997) pp. 269-277.

J. Gonzalez et al., "Cell-Based Assays and Instrumentation for Screening Ion-Channel Targets", DDT, vol. 4, No. 9 (Sep. 1999) pp. 431-439.

G. Turcatti et al., "Probing the Structure and Function of the Tachykinin Neurokinin-2 Receptor Through Biosynthetic Incorporation of Fluorescent Amino Acids at Specific Sites", The Journal of Biological Chemistry, vol. 271, No. 33 (Aug. 16, 1996) pp. 19991-19998.

F. Ka-Ming Chan et al., "Fluorescence Resonance Energy Transfer Analysis of Cell Surface Receptor Interactions and Signaling Using Spectral Variants of the Green Fluorescent Protein", Cytometry, vol. 44 (2001) pp. 361-368.

D. Maurel et al., "Cell Surface Detection of Membrane Protein Interaction with Homogeneous Time-Resolved Fluorescence Resonance Energy Transfer Technology", Analytical Biochemistry, vol. 329 (2004) pp. 253-262.

J.P. Pin et al., "Activation Mechanism of the Heterodimeric $GABA_B$ Receptor", Biochemical Pharmacology, vol. 68 (2004) pp. 1565-1572.

H. Bazin et al., "Homogeneous Time Resolved Fluorescence Resonance Energy Transfer Using Rare Earth Cryptates as a Tool for Probing Molecular Interactions in Biology", Spectrochimica Acta Part A, vol. 57 (2001) pp. 2197-2211.

A. Chollet et al., "Biophysical Approaches to G Protein-Coupled Receptors : Structure, Function and Dynamics", Journal of Computer-Aided Molecular Design, vol. 13 (1999) pp. 209-219.

G. Mathis, "Rare Earth Cryptates and Homogeneous Fluoroimmunoassays with Human Sera", Clin. Chem., vol. 39, No. 9 (1993) pp. 1953-1959.

G. Hermanson, "The Chemistry of Reactive Groups", Bio. Techniques, University of Michigan Academic Press. Chapter 2 (1996) pp. 137-166.

E. Guignet et al., "Reversible Site-Selective Labeling of Membrane Proteins in Live Cells", Nature Biotechnology, vol. 22, No. 4 (Apr. 2004) pp. 440-444.

M. Wilson et al., "Fluorescence Resonance Energy Transfer Studies on the Interaction Between the Lactate Transporter MCT1 and CD147 Provide Information on the Topology and Stoichiometry of the Complex in Situ", The Journal of Biological Chemistry, vol. 277, No. 5 (Feb. 1, 2002) pp. 3666-3672.

J. Liu et al., "Molecular Determinants Involved in the Allosteric Control of Agonist Affinity in the $GABA_B$ Receptor by the $GABA_{B2}$ Subunit", The Journal of Biological Chemistry, vol. 279, No. 16 (Apr. 16, 2004) pp. 15824-15830.

S. Mehier-Humbert et al., "Physical Methods for Gene Transfer : Improving the Kinetics of Gene Delivery into Cells", Advanced Drug Delivery Reviews, vol. 57 (2005) pp. 733-753.

M. Golzio et al., "In Vitro and In Vivo Electric Field-Mediated Permeabilization, Gene Transfer, and Expression", Methods, vol. 33 (2004) pp. 126-135.

J. O'Brien et al., "Biolistic and Diolistic Transfection : Using the Gene Gun to Deliver DNA and Lipophilic Dyes into Mammalian Cells", Methods, vol. 33 (2004) pp. 121-125.

L. Jacobsen et al., "FuGENE 6 Transfection Reagent : The Gentle Power", Methods, vol. 33 (2004) pp. 104-112.

A. Peel, "Transfection of Mammalian Cells", Methods, vol. 33 (2004) pp. 93-94.

B. Dalby et al., "Advanced Transfection with Lipofectamine 2000 Reagent : Primary Neurons, siRNA, and High-Throughput Applications", Methods, vol. 33 (2004) pp. 95-103.

P. Grandi et al., "Targeting HSV Amplicon Vectors", Methods, vol. 33 (2004) pp. 179-186.

A. Amalfitano, "Utilization of Adenovirus Vectors for Multiple Gene Transfer Applications", Methods, vol. 33 (2004) pp. 173-178.

A. Blesch, "Lentiviral and MLV Based Retroviral Vectors for Ex Vivo and in Vivo Gene Transfer", Methods, vol. 33 (2004) pp. 164-172.

O. Gresch et al., "New Non-Viral Method for Gene Transfer into Primary Cells", Methods, vol. 33 (2004) pp. 151-163.

C. Zhang et al., "Polyethylenimine Strategies for Plasmid Delivery to Brain-Derived Cells", Methods, vol. 33 (2004) pp. 144-150.

M. Jordan et al., "Transfection of Adherent and Suspended Cells by Calcium Phosphate", Methods, vol. 33 (2004) pp. 136-143.

J. Lerche Hansen et al., "Functional Consequences of 7TM Receptor Dimerization", European Journal of Pharmaceutical Sciences, vol. 23 (2004) pp. 301-317.

C.D. Rios et al., "G-Protein-Coupled Receptor Dimerization : Modulation of Receptor Function", Pharmacology & Therapeutics, vol. 92 (2001) pp. 71-87.

M.L. Parmentier et al., "A Model for the Functioning of Family 3 GPCRs", Trends in Pharmacological Sciences, vol. 23, No. 6 (Jun. 2002) pp. 268-274.

B. Lew et al., "Protein Splicing in Vitro with a Semisynthetic Two-Component Minimal Intein", The Journal of Biological Chemistry, vol. 273, No. 26 (Jun. 26, 1998) pp. 15887-15890.

S. Terrillon et al., "Roles of G-Protein-Coupled Receptor Dimerization", EMBO Reports, vol. 5 (2004) pp. 30-34.

G. Vassart et al., "A Molecular Dissection of the Glycoprotein Hormone Receptors", TRENDS in Biochemical Sciences, vol. 29, No. 3 (Mar. 2004) pp. 119-126.

S. Bulenger et al., "Emerging Role of Homo- and Heterodimerization in G-Protein- Coupled Receptor Biosynthesis and Maturation", TRENDS in Pharmacological Sciences, vol. 26, No. 3 (Mar. 2005) pp. 131-137.

G. Milligan, "G Protein-Coupled Receptor Dimerization: Function and Ligand Pharmacology", Molecular Pharmacology, vol. 66, No. 1 (2004) pp. 1-7.

I. Giriat et al., "Protein Semi-Synthesis in Living Cells", J. Am. Chem. Soc., vol. 125 (2003) pp. 7180-7181.

M.A. Prado et al., "Receptor Component Protein (RCP): A Member of a Multi-Protein Complex Required for G-Protein-Coupled Signal Transduction", Biochemical Society Transactions, vol. 30, Part 4 (2002) pp. 460-464.

C. Bissantz et al., "Conformational Changes of G Protein-Coupled Receptors During Their Activation by Agonist Binding", vol. 23, No. 2 & 3 (2003) pp. 123-153.

Sambrook, Fritsch, Maniatis—Molecular Cloning—A Laboratory Manual—Second Edition—Book 3 Chapter 16 (1988) pp. 16.3-16.72.

J.R. Lakowicz, "Energy Transfer", Principles of Fluorescence Spectroscopy, $3^{rd}$ Edition, Chapter 13 (2008) pp. 443-453.

* cited by examiner

HA-GB1+FLAG-GB2 :

HA-GB1+FLAG-GB2-YFP :

METHOD OF REVEALING A BIOLOGICAL PROCESS USING A FRET MEASUREMENT

FIELD OF THE INVENTION

The present invention relates to the field of cell biology and more particularly to the study of the interactions between biological entities or between the different constituent parts of these entities, optionally in the presence of potential ligands, for the purpose of elucidating the biological or pathological processes and screening new drugs.

Attempts are increasingly being made to study the biological or pathological processes within membrane preparations or live cells, and this is frequently done using fluorescence measurement tests, particularly fluorescence tests which measure the non-radiative resonance energy transfer between a donor fluorophore and an acceptor fluorophore.

After luminous excitation at the excitation wavelength of the donor fluorophore, an energy transfer takes place between the donor fluorophore and the acceptor fluorophore if they are close to one another; this energy transfer is characterized by an emission of light by the acceptor (FRET signal), which can be measured with a fluorimeter.

The use of rare earth chelates or cryptates as donor fluorophores has made it possible to develop the technique known as HTRF® (Homogeneous Time Resolved Fluorescence) (cf. in particular "Homogeneous time resolved fluorescence energy transfer using rare earth cryptates as a tool for probing molecular interactions in biology", Spectrochimica Acta Part A 57 (2001) 2197-2211); this technique has numerous advantages which have already enabled several applications in the field of in vitro diagnostics and in the field of high-throughput screening in the pharmaceutical industry.

STATE OF THE ART

The technology of time resolved FRET for detecting the interactions between membrane proteins on the surface of cells has been described by Damien Maurel et al. (cf. document 1). J. P. Pin et al. and Jianfeng Liu et al. have studied the $GABA_B$ receptor by the technology of time resolved FRET (cf. documents 2 and 3).

In all these studies, the members of the pair of FRET partners are located in the extracellular medium.

It has been proposed to study ion channels, which are important targets for drugs, by means of a FRET system (cf. documents 4, 5 and 6). In these studies the donor fluorophore is generally coumarin bonded to a lipid chain, which is bound to the extracellular part of the plasma membrane of the cells, and the acceptor is a dye of the oxonol type, which can migrate into the plasma membrane depending on the membrane potential. In these studies, therefore, the fluorophores are never located on either side of the plasma membrane.

Turcatti et al. and Chollet et al. (cf. documents 7 and 8) have studied the $NK_2$ receptor by means of a FRET system using membrane preparations of oocytes, in which the acceptor fluorophore is a ligand coupled with rhodamine and the donor fluorophore is nitrobenzoxadiazole (NBD) incorporated specifically at precise sites of the $NK_2$ receptor which are located on either side of the plasma membrane.

F. Chan et al. (cf. document 9) describe the use of FRET between variants of the green fluorescent protein (GFP) as donor fluorophore in order to study the interactions between receptors on the cell surface. Various receptor constructs have been produced with the blue fluorescent protein (CFP) or the yellow fluorescent protein (YFP) as acceptor fluorophore on the extracellular or intracellular parts.

The experiments performed in order to detect the association of the receptors show that a FRET is detected only when the acceptor fluorophore and the donor fluorophore are on the intracellular part or the extracellular part of the receptor. On the other hand, it has not been possible to detect a FRET when one of the fluorophores is on the intracellular part and the other fluorophore is on the extracellular part of the receptor, i.e. when the fluorophores are on either side of the plasma membrane (cf. FIG. 4 of said document).

The team of M. C. Wilson et al. (cf. document 10) has also found, when studying the interaction between the lactate transporter MCT1 and the glycoprotein CD147 on the surface of COS cells, that a FRET is only detectable when the donor and the acceptor are located in the intracellular part of MCT1 and CD147. On the other hand, none of the constructs in which the donor fluorophore and the acceptor fluorophore are on either side of the plasma membrane gives a FRET signal (cf. Table 1 of said document).

Therefore, these FRET systems do not enable the interactions between the biological entities to be detected when they are on either side of the plasma membrane. Now, it is known that biological processes are activated or inhibited by the transfer of information from the outside of the cell to the inside of the cell.

It therefore proves valuable and highly desirable to be able to detect directly the interactions caused by a biological entity or a ligand in the extracellular medium on a biological entity in the intracellular medium of living cells.

It has been proposed by Guignet et al. (cf. document 11) to selectively label the membrane proteins in living cells using a donor fluorophore, in this instance a green fluorescent protein, and a non-fluorescent acceptor, and to measure the disappearance of the fluorescence of the donor, it being possible for the donor and acceptor to be on either side of the plasma membrane.

This method of measurement does not make it possible to distinguish between a decrease in fluorescence due to the energy transfer between the donor and the acceptor and a decrease in fluorescence due to variations in the optical properties of the medium in which the energy transfer is measured.

Such a system can therefore be used only when the optical variations are considerable.

WO 03/005028 describes a method of selecting active agents that is based on the measurement of luminescence modifications associated with changes in distance between two luminophores, one of which is located in the cell membrane, while the other may or may not be engaged with the cell membrane, depending on its biological activity. The variation in luminescence can be determined by measuring variations in FRET between the two luminophores. The luminophores used in WO 03/005028 are on the one hand a fluorescent or luminescent intermediate agent produced by the cell system, and on the other hand a lipophilic luminophore which is compatible with natural cell membranes and which produces a coupling of fluorescence with said intermediate agent. WO 03/005028 does not describe systems involving a transmembrane energy transfer, since one of the luminophores is located inside the plasma membrane, either in its outer layer or in its inner layer. Thus the method described in said patent application does not make it possible to study biological phenomena which would result in a totally transmembrane energy transfer, i.e. one that crosses the two layers, inner and outer, of the lipid bilayer. Also, insofar as one of the luminophores is a lipid or is coupled with a lipid distributed homogeneously throughout the plasma membrane, this method does not make it possible to study specific biological phenomena.

Hence there is a genuine need for means of revealing biological processes which result from the interaction between biological molecules or constituent parts of these molecules when they are in a measurement medium containing a plasma membrane or any other lipid membrane.

SUMMARY OF THE INVENTION

It has now been found that it is possible to reveal a biological process in a cell system by means of a FRET measurement using, as the donor fluorophore, a fluorophore which has a long lifetime, the donor and acceptor fluorophores being coupled with biological entities and said donor and acceptor fluorophores being located on either side of a lipid membrane.

The present invention thus relates to a method of revealing a biological process using a FRET measurement, which consists in:

incorporating, into a measurement medium containing a lipid membrane, a biological entity X coupled with a first member of a pair of FRET partners and a second biological entity Y coupled with the second member of the pair of FRET partners, the energy-donating member of the pair of FRET partners having a long lifetime and the members of said pair of FRET partners being located on either side of the lipid membrane;

exciting the measurement medium at the excitation wavelength of the energy-donating member; and measuring the FRET signal or the variations in said signal emitted in said culture medium.

In one variant, the method according to the invention comprises a step for stimulating the measurement medium, it being possible for said stimulation to be an electrical, mechanical or thermal stimulation. It is in fact known that such stimulations can result in the activation of biological processes in the cell. Thus a change in temperature of the medium can modify the conformation of certain transmembrane proteins, such as the thermoreceptors, and these modifications can be studied by means of the procedure according to the invention. Likewise, certain signaling pathways can be triggered by the activation of mechanoreceptors or else by variations in the membrane potential. These signaling pathways can be studied by selective labeling of the biological entities X and Y involved in these processes and by measurement of the variations in transmembrane FRET after stimulation.

In another variant, the method of the invention comprises a chemical stimulation step; in this case the procedure according to the invention is carried out in the presence of a compound whose effect on the cells it is desired to test e.g. whether it is agonistic or antagonistic towards a membrane receptor consisting of one of the biological entities X or Y. The method according to the invention is therefore very useful for screening banks of test compounds originating e.g. from syntheses by combinatorial chemistry. In fact, a possible biological effect of the test compound on the biological process studied can be revealed by measuring the variation in the transmembrane FRET between the biological entities X and Y involved in a given biological process, in the presence or absence of the test compound.

The biological processes which can be revealed by the method of the invention are numerous and differ according to the nature of the biological entities used.

The following are examples of these biological processes:
the phenomena of dimerization of two intrinsic proteins, e.g. the homodimerization or heterodimerization of transmembrane receptors;

the phenomenon of translocation of a cytosoluble compound to or from a membrane protein;

the detection of ligands specific for membrane receptors and the screening of drugs; and the changes in three-dimensional structure of a transmembrane receptor in the presence of a ligand, or the changes in structure of protein complexes.

The coupling of the biological entities with one of the members of a pair of FRET partners is effected either directly by means of one or more covalent bonds according to techniques well known to those skilled in the art (Bioconjugate Techniques, G. T. Hermanson, Academic Press, 1996), or indirectly via binding partners of the following types: tag/anti-tag antibody, antigen/antibody, avidin or streptavidin/biotin, hapten/antibody.

The FRET signal is measured by the conventional methods well known to those skilled in the art, as described e.g. by Mathis G., "Rare Earth Cryptates and Homogeneous Fluoroimmunoassays with Human Sera", Clin. Chem. 1993, 39, no. 9, 1953-1959.

For example, the variations in the FRET signal can be measured quantitatively by means of conventional fluorescence detectors that are commonly used by those skilled in the art in laboratories specialized in high-throughput screening (e.g. with the Rubystar fluorimeter from BMG labs).

Measurement of the variations in the FRET signal makes it possible to detect a biological process directly and provides a solution suited to searching for molecules that modulate these processes in high-throughput screening.

DETAILED DESCRIPTION OF THE INVENTION

1) Measurement Medium

The measurement medium consists of a biological medium containing a lipid membrane.

Most of the time this biological medium is a cell culture, i.e. it contains live cells in a culture medium. Broadly speaking, "biological medium" is understood as meaning any preparation comprising cell tissues, live or dead cells or cell lyzates, or reconstituted biological systems comprising the proteins necessary for studying a given biochemical process.

"Lipid membrane" is understood in the present description as meaning the plasma membrane, the endoplasmic reticulum membrane, the mitochondrial double membrane, a lysosomal membrane, the nuclear membrane or the Golgi vesicle membrane. Advantageously, the lipid membrane is the plasma membrane and the measurement medium is a preparation of transfected cells.

In the present description, "preparation of transfected cells" is understood as meaning the transfected cells themselves, the transfected cells permeabilized by techniques well known to those skilled in the art, especially using detergents such as Triton X100, and the membrane preparations of transfected cells.

The cells can be stably transfected, i.e. the sequences coding for the biological entities X and Y are integrated into the DNA of the cells.

The cells can also be transiently transfected with the aid of a plasmid-type expression vector containing the nucleic acid sequence coding for said biological entities X and Y.

Cell transfection techniques, which are well known to those skilled in the art, are described e.g. in the work by Sambrook et al., Molecular Cloning: A Laboratory Manual; 2nd edition; Cold Spring Harbor Laboratory, Cold Spring Harbor, N.Y. (1989), and by Mehier-Humbert S., Guy R. H., "Advanced Drug Delivery Reviews" (2005) Physical methods for gene transfer: improving the kinetics of gene delivery into cells, 57 (5) pp 733-753. In addition, transfections into mammalian cells are described in "Methods" Volume 33 Issue 2 pp 93-186 (June 2004).

The cells used are generally mammalian cells such as HEK 293 cells.

The biological entities X and Y can also be incorporated into the cells by permeabilization of the latter, e.g. by controlled treatment with a detergent such as Triton X100.

2) Biological Entities

The biological entities X and Y are selected from intrinsic or extrinsic membrane proteins, transmembrane proteins such as transmembrane receptors, cytosoluble compounds, organic or biological compounds belonging to a bank of compounds whose effect on cells it is desired to test (these are referred to hereafter as "ligands"), and antibodies.

Examples of transmembrane proteins are receptors such as, in particular, seven-domain transmembrane receptors coupled with G proteins (hereafter called GPCRs), which are involved in numerous pathological processes. In fact, GPCRs are transmembrane proteins responsible for recognizing and transferring information from the outside to the inside of the cell. These proteins represent important therapeutic targets and more than 50% of current drugs target these receptors or their transduction cascade.

"Intrinsic membrane compounds" are understood as meaning compounds located in a lipid membrane, e.g. the plasma membrane. Examples of intrinsic membrane compounds which may be mentioned are transmembrane proteins, transmembrane receptors such as GPCRs, channel proteins, transport or exchange proteins, proteins which stabilize the structure of the plasma membrane, immunoglobulins, hormone receptors, receptors with tyrosine kinase activity, and enzymes such as adenylylcyclase.

"Extrinsic membrane compounds" are understood as meaning compounds located on one or other side of a lipid membrane. Examples which may be mentioned are anchoring proteins located on the outer face of the plasma membrane, enzymes located on the inner face of the plasma membrane, such as phospholipases, proteins involved in signal transduction processes, such as heterotrimeric G proteins, kinases of receptors coupled with G proteins (GRK), arresting, proteins that interact with arrestins to form submembranous scaffolding such as traffic proteins [clathrin, AP2 (adaptor protein-2), NSF (nucleotide exchange factor for ARF, ARF being the ADP-ribosylation factor)], small G proteins and nucleotide exchange factors (ARF6, ARNO, RhoA, etc.), signaling proteins (MAP kinases, MAP denoting mitogenic activated proteins, c-Src, Yes, Mdm2, etc.), phosphodiesterases (PDE4, etc.) and protein phosphatases (PP2A, etc.).

3) Members of the Pair of FRET Partners

The pair of FRET partners comprises a donor fluorophore and an acceptor fluorophore, one of the fluorophores being a fluorophore with a long lifetime, i.e. a lifetime in excess of 100 ns, preferably of between 100 ns and 5000 μs and particularly preferably of between 100 and 3000 μs.

Examples of fluorophores with a long lifetime which are suitable for the purposes of the invention are rare earth complexes, particularly terbium and europium complexes.

Rare earth complexes are known compounds and are described e.g. in U.S. Pat. No. 4,761,481, U.S. Pat. No. 5,032,677, U.S. Pat. No. 5,055,578, U.S. Pat. No. 5,106,957, U.S. Pat. No. 5,116,989, U.S. Pat. No. 4,761,481, U.S. Pat. No. 4,801,722, U.S. Pat. No. 4,794,191, U.S. Pat. No. 4,637,988, U.S. Pat. No. 4,670,572, U.S. Pat. No. 4,837,169 and U.S. Pat. No. 4,859,777. Other chelates are made up of a nonadentate ligand such as terpyridine (cf. EP 403 593, U.S. Pat. No. 5,324,825, U.S. Pat. No. 5,202,423, U.S. Pat. No. 5,316,909).

Advantageously, the rare earth complex is a chelate or a cryptate. When the rare earth is europium, the rare earth complex is preferably a rare earth cryptate with a pyridine unit or, particularly preferably, with a pyridine-bipyridine unit.

Rare earth cryptates are described in patents EP 0 180 492 and EP 0 601 113 and patent application WO 01/96 877.

Very particularly preferred among these cryptates are those with a pyridine bipyridine unit of the formula:

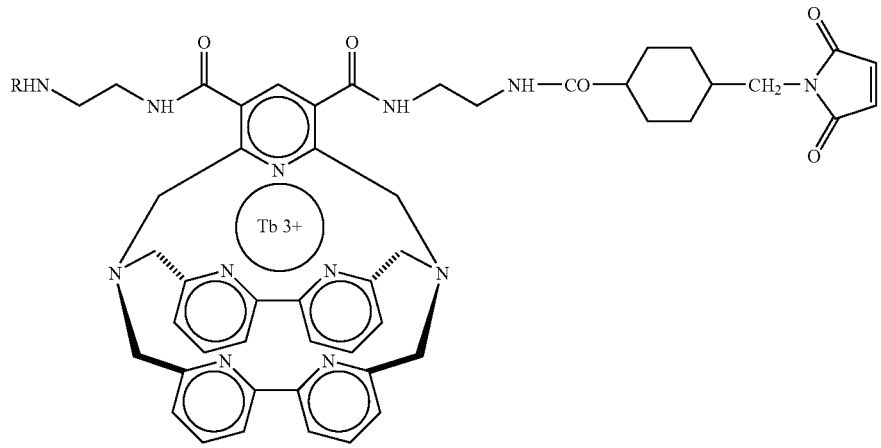

The other fluorophore belonging to the pair of FRET partners is a fluorescent substance selected from rhodamines, cyanins, squaraines, fluorophores known as BODIPYs (difluoroboradiazaindacenes), fluoresceins, fluorophores known as AlexaFluor, quantum dots, fluorescent proteins such as the green fluorescent protein (GFP) or its variants, fluorescent proteins extracted from corals, and phycobiliproteins such as B-phycoerythrin, R-phycoerythrin, C-phycocyanin and allophycocyanins, particularly those known as XL665.

Selection of the members of a pair of FRET partners is within the capability of those skilled in the art Reference may be made in this connection to the work by Lakowicz, Principles of fluorescence spectroscopy, 2nd edition, Kluwer Academic/Plenum Publishers, NY (1999).

"Donor fluorophore/acceptor fluorophore pair" is understood in the present description as meaning pairs of fluorophores for which the absorption spectrum of the acceptor at least partially overlaps the emission spectrum of the donor so that an energy compatibility exists between the two molecules. Preferably, this energy compatibility results in a Förster radius (donor/acceptor distance for which the transfer efficiency is equal to 50%) greater than 4 nm n.

Pairs of FRET partners which are particularly appropriate for the purposes of the invention are the pairs below in which the donor is a terbium cryptate and the acceptor is a fluorescent protein such as YFP. Other pairs of FRET partners which are appropriate for the purposes of the invention are pairs in which the donor is a europium cryptate and the acceptor is either crosslinked allophycocyanin, known under the trade name XL665, or the fluorophore d2, marketed by CIS bio international, or AlexaFluor 647.

4) Coupling of the Members of the Pair of Fret Partners (Fluorophores)

As indicated previously, the coupling of the members of a pair of FRET partners with the biological entities X or Y is effected either directly by means of one or more covalent bonds, or indirectly via binding partners of the following types: tag/anti-tag antibody, antigen/antibody, avidin or streptavidin/biotin, hapten/antibody.

Direct coupling of the fluorophores can be effected:

1) by expressing a fusion protein between said biological entities X or Y and a fluorescent protein;

2) by expressing a fussion protein between said biological entities X or Y and a protein with irreversible enzymatic activity (commonly called a suicide enzyme), which transfers the fluorophore onto said biological entity X or Y; or 3) by splicing with an intein.

This technique of coupling by splicing with an intein is described e.g. in The Journal of Biological Chemistry, vol. 273, no. 26, pp 15887-15890, 26 Jun. 1998, and J. Am. Chem. Soc. 2003, 125, 7180-7181.

Indirect coupling of the fluorophores can be effected:

1) via a "ligand/biological entity" or "tag/anti-tag" pair;

2) by expressing the native biological entities X or Y, in which case the fluorescent compounds are conjugated with an antibody that specifically recognizes the biological entities; or 3) by expressing the biological entities coupled with a suicide enzyme, which transfers a tag onto said biological entities.

These methods of direct and indirect coupling of fluorophores use the recombinant DNA techniques well known to those skilled in the art.

The direct coupling of a fluorophore by expressing a fusion protein between said biological entities X or Y and a protein with irreversible enzymatic activity advantageously uses an $O^6$-alkylguanine-DNA alkyltransferase (AGT) (cf. WO 02/083937) or a dehalogenase as the protein with irreversible enzymatic activity.

In this case the cells are transfected with a nucleic acid coding for one of said biological entities and with a nucleic acid coding for said protein with irreversible enzymatic activity. They are then brought into contact with the substrate specific for said protein with enzymatic activity, carrying the fluorophore which it is desired to couple with the receptor or one of the subunits Gα or Gβγ.

In the indirect coupling of a fluorophore via a "ligand/receptor" or "tag/anti-tag" pair, a fusion protein between one of said biological entities and a peptide sequence called a "tag" is expressed, the fluorescent compounds in this case being conjugated with an antibody that specifically recognizes the tag. The peptide sequences are those commonly used in molecular biology, e.g. the "Myc" or "FLAG" tags mentioned below.

The term "ligand/receptor pair" denotes two binding partners such as the following pairs: hapten/antibody; DNP/anti-DNP antibody, in which DNP represents dinitrophenol; GST/anti-GST antibody, in which GST represents glutathione S-transferase; biotin/avidin; 6HIS/anti-6HIS antibody, in which 6HIS is a peptide consisting of 6 histidines; Myc/anti-Myc antibody, in which Myc is a peptide consisting of amino acids 410-419 of the human Myc protein; FLAG®/anti-FLAG® antibody, in which FLAG® is a peptide consisting of the 8 amino acids DYKDDDDK; HA/anti-HA antibody, in which HA is an epitope of influenza hemagglutinin consisting of the 9 amino acids YPYDVPDYA.

These pairs, commonly known as "tag/anti-tag" pairs, are well known to those skilled in the art and are commercially available.

5) Measurement of the FRET Signal

The measured FRET signal can be directly correlated with the biological phenomenon studied: in fact, the level of energy transfer between the donor fluorescent compound and the acceptor fluorescent compound is proportional to the reciprocal of the distance between these compounds to the power 6. For the donor/acceptor pairs commonly used by those skilled in the art, the distance Ro (corresponding to a transfer efficiency of 50%) is in the order of a nanometer, making FRET a preferred tool for studying biological interactions.

The variation in the FRET signal depends on the type of biological phenomenon, but, in general, as the donor and acceptor fluorescent compounds move closer together, an energy transfer is caused from the donor compound to the acceptor compound, resulting in a decrease in the fluorescence signal emitted by the donor compound and an increase in the signal emitted by the acceptor compound, and vice-versa. The majority of biological phenomena involving interactions between different partners will therefore be able to be studied by measuring the change in FRET between 2 fluorescent compounds coupled with compounds which will be at a greater or lesser distance, depending on the biological phenomenon in question.

The FRET signal can be measured in different ways: measurement of the fluorescence emitted by the donor alone, by the acceptor alone or by the donor and the acceptor, or measurement of the variation in the polarization of the light emitted in the medium by the acceptor as a result of FRET. One can also include measurement of FRET by observing the variation in the lifetime of the donor, which is facilitated by using a donor with a long fluorescence lifetime, such as rare earth complexes (especially on simple equipment like plate readers).

Furthermore, the FRET signal can be measured at a precise instant or at regular intervals, making it possible to study its change over time and thereby to investigate the kinetics of the biological process studied.

6) Biological Processes

Depending on the nature of the biological entities used, the method of the invention makes it possible to detect different biological processes, which are explained in detail below. In all cases these processes are studied by measuring a transmembrane FRET between 2 biological entities involved in said processes.

a) Modification of the Three-Dimensional Structure of a Transmembrane Receptor in the Presence of a Test Ligand It is known that the three-dimensional structure of proteins can vary during biological phenomena, an example being the binding of a ligand to its receptor. The variations in the structure of transmembrane proteins in response to binding with their ligand, as is the case e.g. of the GABA receptor or the glutamate receptor (GluR), may be very particularly mentioned (Parmentier M. L., Prezeau L., Bockaert J., Pin J. P. (2002) A model for the functioning of family 3 GPCRs. Trends Pharmacol. Sci. 23 (6): 268-74; Bissantz C. (2003) Conformational changes of G protein-coupled receptors during their activation by agonist binding. J. Recept. Signal Transduct. Res. 23 (2-3); 123-53).

If the biological entities X and Y are one and the same transmembrane receptor and the lipid membrane is the plasma membrane, the variation in the FRET signal in the presence of a test ligand will be indicative of a modification of the three-dimensional structure of said receptor caused by the test ligand.

The method according to the invention can also be carried out in order to study variations in the structures of protein complexes: this is the case e.g. of RCP (receptor component protein)/G protein complexes, where the compound X is an RCP and the compound Y is a G protein, the compounds X and Y forming a protein complex. When the compound X is activated, the compounds X and Y continue to interact, but the structural modifications resulting from the activation of X may be detected by measuring the FRET signal (cf. Prado M. A., Evans-Bain B., Dickerson I. M. (2002) Receptor component protein (RCP): a member of a multi-protein complex required for G-protein-coupled signal transduction. Biochem. Soc. Trans. 30 (4): 460-4).

b) Phenomenon of Dimerization of Intrinsic Membrane Proteins

In the case where the two biological entities X and Y are two transmembrane proteins and the lipid membrane is the plasma membrane, the variation in the FRET signal in the presence or absence of a test compound will be indicative of an interaction between said proteins.

Such interactions may be constitutive or may be induced by a biological event.

It is known that the function of certain membrane receptors is modulated by their dimerization. This dimerization can be a homodimerization if the two receptors are identical, or a heterodimerization if the receptors are different. The following may be mentioned as examples of such receptors across the three known families of receptors: the $GABA_B$ receptor, the EGF receptor, the metabotropic glutamate receptors (mGluRs), the vasopressin receptors, the β-adrenergic receptors, the opiate receptors, the chemokine receptors, the melatonin receptors and the glycoprotein hormone receptors. This dimerization phenomenon is known to those skilled in the art and is widely described in the literature (cf., for example: Sebastien Bulenger, Stefano Marullo and Michel Bouvier (2005) Emerging role of homo- and hetero-dimerization in G-protein coupled receptor biosynthesis and maturation. Trends in Pharmacological Sciences, vol. 26 (3) pp 131-37; Hansen J. L., Sheikh S. P. (2004) Functional consequences of 7™ receptor dimerization. Eur. J. Pharm. Sci. 23 (4-5): 301-17; Vassart G., Pardo L., Costagliola S. (2004) A molecular dissection of the glycoprotein hormone receptors. Trends Biochem. Sci. 29 (3): 119-26; Milligan G. (2004) G protein-coupled receptor dimerization: function and ligand pharmacology. Mol. Pharmacol. 66 (1) 1-7; Terrillon S. and Bouvier M. (2004) Roles of G-protein-coupled receptor dimerization. EMBO Rep. 5, 30-34; Rios C. D., Jordan B. A., Gomes I., Devi L. A. (2001) G-protein-coupled receptor dimerization: modulation of receptor function. Pharmacol, Ther. 92 (2-3): 71-87.

c) Phenomenon of Translocation of a Cytosoluble Compound to the Plasma Membrane

If the biological entity X is a cytosoluble compound and the entity Y is an intrinsic or extrinsic membrane compound, the variation in the FRET signal will be indicative of a phenomenon of translocation of said cytosoluble compound to or from said membrane protein.

An example of such phenomena which may be mentioned is the translocation of arrestin molecules to the plasma membrane, which participates in the phenomenon of internalization of transmembrane proteins, especially certain receptors coupled with C proteins. The phenomenon of translocation of G proteins to or from membrane proteins, such as receptors coupled with G proteins, may also be mentioned.

d) Binding of a Test Ligand to a Transmembrane Receptor

If the lipid membrane is the plasma membrane and if the biological entity X is a transmembrane receptor located on the plasma membrane and labeled in its intracellular part with a member of a pair of donor/acceptor fluorescent compounds and the biological entity Y is a potential ligand for said transmembrane receptor, forming part of a bank of test compounds and labeled with the other member of the pair of donor/acceptor fluorescent compounds, the variation in the FRET signal will be indicative of the binding of said ligand to the receptor. This process is particularly advantageous for screening banks of compounds derived from combinatorial chemistry.

The same type of process can be carried out by a so-called competitive method: in this case X is a transmembrane receptor located on the plasma membrane and labeled in its intracellular part with a member of a pair of donor/acceptor fluorescent compounds and Y is a known ligand for said transmembrane receptor which is labeled with the other member of the pair of donor/acceptor fluorescent compounds; a test compound is added to the measurement medium and the variation in the FRET signal is determined in the presence and absence of this compound. If the test compound is in fact capable of binding to the receptor X, it enters into competition with the ligand Y in order to bind to the receptor X, resulting in a variation in the transmembrane FRET signal.

This process is also advantageously used for screening banks of chemical compounds.

The invention will now be described in greater detail by means of the illustrative but non-limiting Examples below.

Example 1

Molecular Constructs

Figure 1:
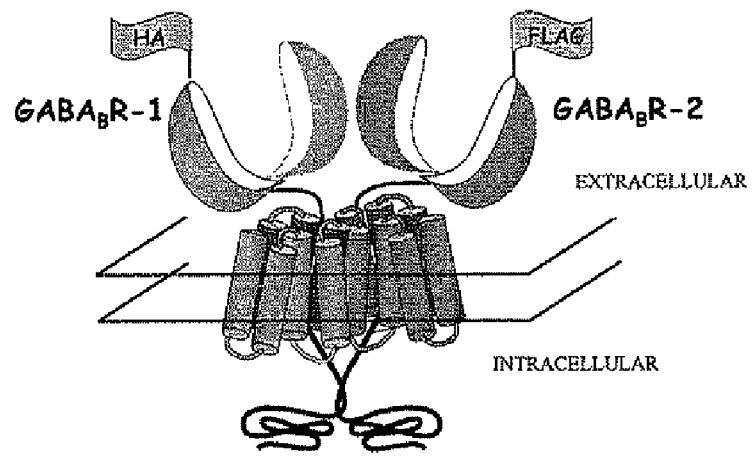
FIG. 1 shows the molecular constructs used to illustrate the invention: a GABAB receptor comprising 2 subunits GABAB1 and GABAB2, tagged with the "HA" or "FLAG" epitopes respectively (top figure), and the GABAB2 subunit being fused with a YFP fluorescent protein in its intracellular domain (bottom figure).
Figure 1:
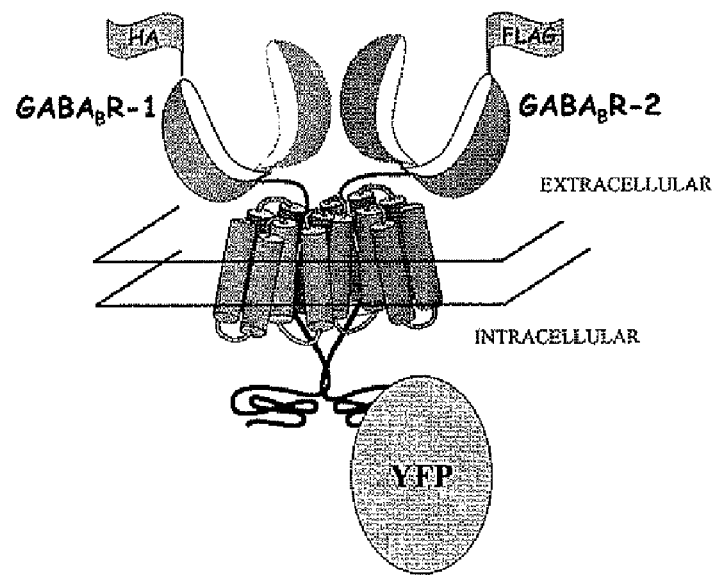

Two constructs, which are illustrated diagrammatically in FIG. 1, were used:
Construct 1: HA-GABAB R-1 ("HA-GB1")+FLAG-GABAB R-2 (FLAG-GB2)
Construct 2: HA-GABAB R-1 ("HA-GB1")+FLAG-GABAB R-2 YFP (FLAG-GB2-YFP)

Example 2

Reagents

The following reagents are used in the experiments described below:
an anti-FLAG antibody labeled with the following terbium cryptate:

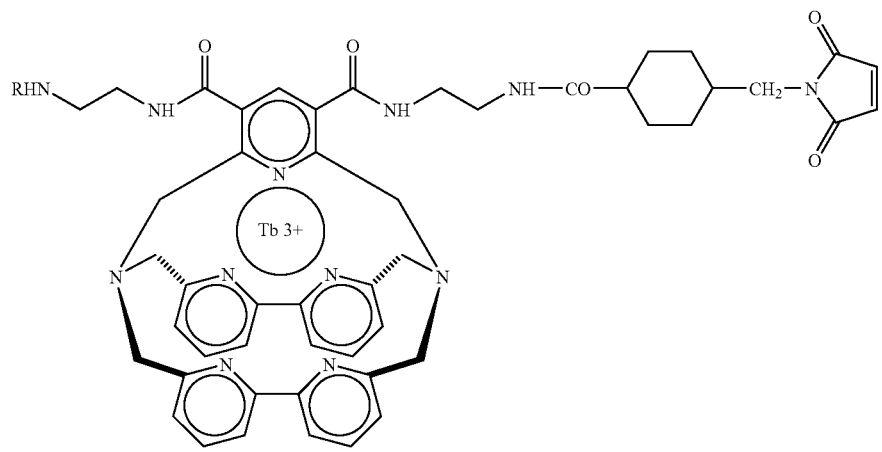

an anti-HA antibody labeled with Alexa 647: the anti-HA antibody was labeled with Alexa 647 succinimidyl ester (Molecular Probes, ref. A-2006). The labeling reaction was carried out in a 0.1 M carbonate buffer, pH 9, for 30 minutes at room temperature, with a molar excess of 4 Alexa 647 per antibody. The excess fluorescent probe which has not reacted with the antibody is removed by exclusion chromatography (Pharmacia Biotech G-25 super fine gel). The final labeling rate of the antibody, determined by means of the absorption spectrum of the conjugate, is 2.6 Alexa 647 per antibody.

Example 3

Measurement of TR-FRET

Figure 2:
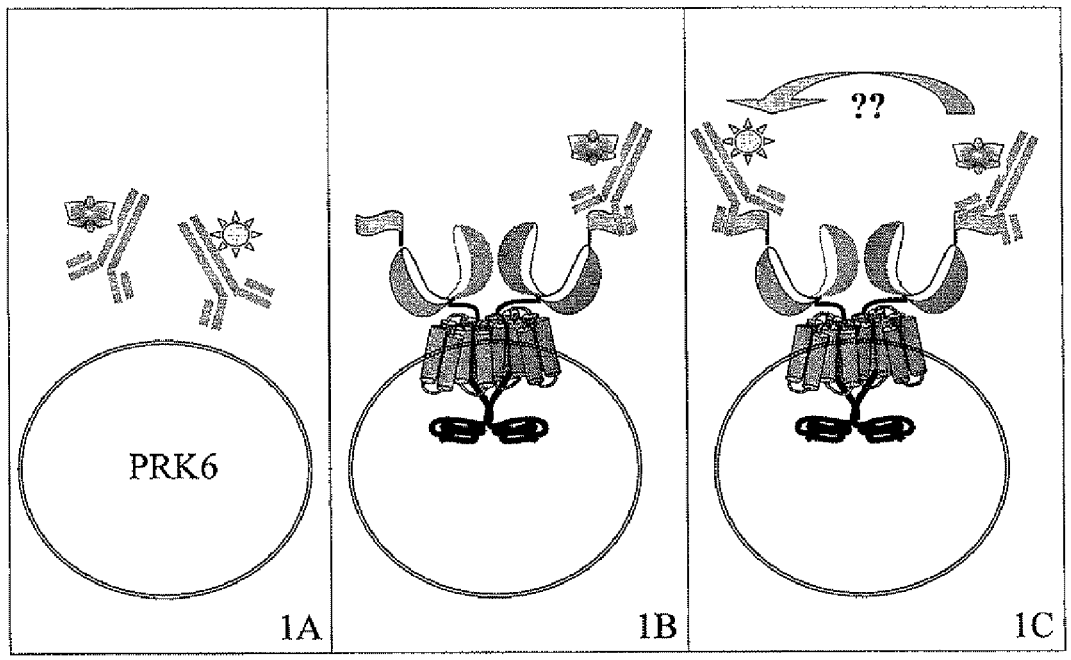
FIG. 2 shows experimental conditions used for fluorescence measurements. The following set-up is indicated by panels 1A, 1B, 1C, 2A, 2B and 2C in FIG. 2:
1A: PRK6 cells+anti-FLAG antibody coupled with a terbium cryptate+anti-HA antibody coupled with Alexa 647;
1B: PRK6 cells expressing HA-GB1 and FLAG-GB2+anti-FLAG/terbium cryptate;
1C: PRK6 cells expressing HA-GB1 and FLAG-GB2+anti-FLAG/terbium cryptate+anti-HA/A647;
2A: PRK6 cells+anti-FLAG/terbium cryptate+anti-HA/A647;
2B: PRK6 cells expressing HA-GB1 and FLAG-GB2-YFP+anti-FLAG/terbium cryptate;
2C: PRK6 cells expressing HA-GB1 and FLAG-GB2-YFP+anti-FLAG/terbium cryptate+anti-HA/A647.
Figure 2:
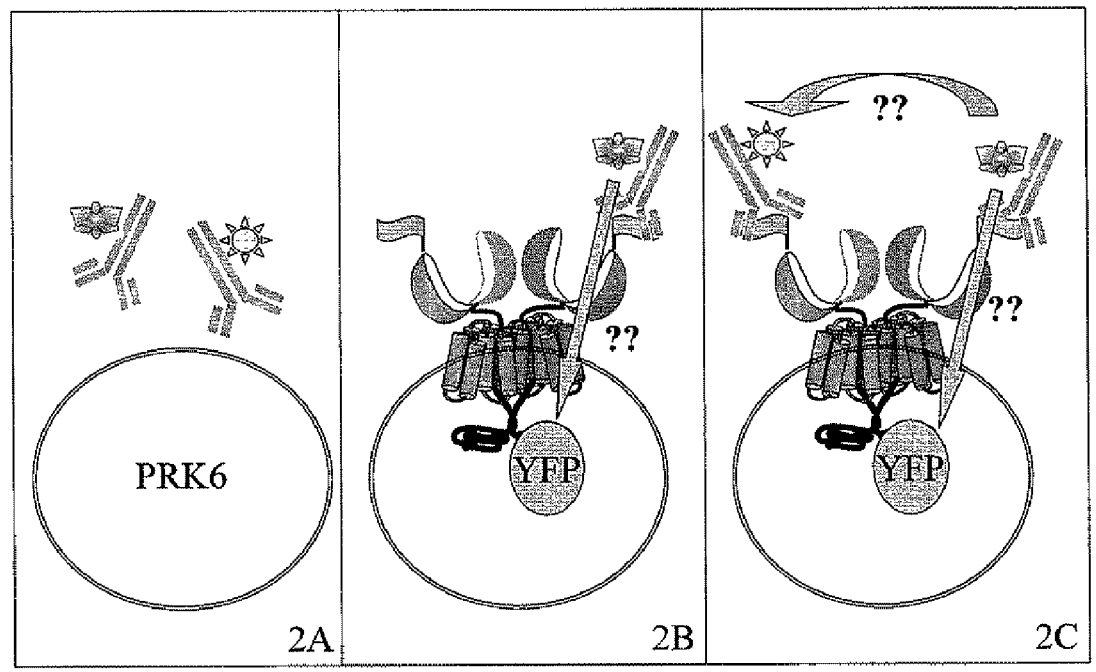

The TR-FRET signal is measured in wells each containing 50,000 or 100,000 cells, said cells containing the molecular constructs described in Example 1 in a final volume of 100 μl, to which the following reagents are added (FIG. 2):
1A: PRK6 cells+anti-FLAG antibody coupled with a terbium cryptate (hereafter "anti-FLAG/terbium cryptate") 1 nM final+anti-HA antibody coupled with Alexa 647 (hereafter "anti-HA/A647") 3 nM final;
1B: PRK6 cells expressing HA-GB1 and FLAG-GB2+anti-FLAG/terbium cryptate 1 nM final;
1C: PRK6 cells expressing HA-GB1 and FLAG-GB2+anti-FLAG/terbium cryptate 1 nM final+anti-HA/A647 3 nM final;
2A: PRK6 cells+anti-FLAG/terbium cryptate 1 nM final+anti-HA/A647 3 nM final;
2B: PRK6 cells expressing HA-GB1 and FLAG-GB2-YFP+anti-FLAG/terbium cryptate 1 nM final;
2C. PRK6 cells expressing HA-GB1 and FLAG-GB2-YFP+anti-FLAG/terbium cryptate 1 nM final+anti-HA/A647 3 nM final.

For each experiment the wells were incubated for 20 h at 4° C. prior to measurement of the fluorescence emitted.

Conditions 1C and 2C make it possible to know whether the expression of the dimer is approximately the same under the 2 test conditions. Conditions 2B and 2C make it possible to reveal a possible FRET between the terbium and YFP. 1A, 1B and 2A are the experimental controls.

Example 4

Measurement of an "Extracellular" FRET Between Terbium Cryptate and A647

After incubation of the cells under conditions 1A, 1B, 2B, 2A, 1C and 2C described in Example 3, the fluorescence emitted by the wells is measured on an Analyst (Molecular Devices), TRF Digital mode, delay 50 μs, integration 400 μs, excitation 330 nm (filter 330/80), dichroic BBUV, emission: detection at 490 nm for terbium and 682 nm for A647. The signal emitted by the acceptor compound is corrected by that emitted by the donor compound by taking a ratio of the measured signals.

Figure 3:
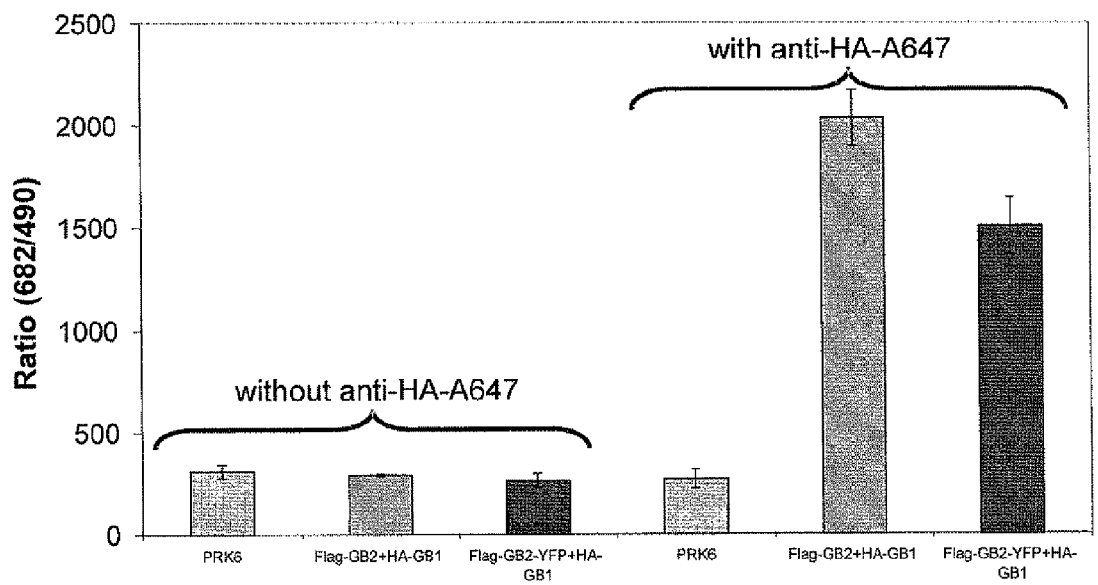
FIG. 3 shows ratio of the luminescence of the acceptor compound (A647, measured at 682 nm) against that of the donor compound (terbium cryptate, measured at 490 nm), in various experimental conditions. This figure confirms the existence of extracellular FRET.

The results presented in FIG. 3 show an increase in the ratio (R) with the dimer GB1/GB2 in the presence of terbium and A647, corresponding to a delta F value of 658%, delta F being calculated as follows:

$$\text{Delta } F = \frac{R_{682/490}(\text{sample}) - R_{682/490}(\text{control})}{R_{682/490}(\text{control})}$$

This experiment shows that an extracellular FRET takes place irrespective of the molecular constructs used, even though a slight decrease in the signal is observed when the dimer contains a YFP (delay F=461%). This can be explained either by a slight difference in the expression level of the receptors, or by the presence of competition between the terbium/A647 and terbium/YFP FRETs.

Similar results are obtained for wells containing 100,000 cells or when the terbium cryptate is replaced with a europium cryptate.

Example 5

Measurement of a Transmembrane FRET Between Terbium Cryptate and YFP

After incubation of the cells under conditions 1A, 1B, 2B, 2A, 1C and 2C described in Example 3, the fluorescence emitted by the wells is measured on an Analyst (Molecular Devices), TRF Digital mode, delay 50 µs, integration 400 µs, excitation 330 nm (filter 330/80), dichroic BBUV, emission: detection at 490 nm for terbium and 520 nm for YFP. The signal emitted by the acceptor compound is corrected by that emitted by the donor compound by taking a ratio of the measured signals.

Figure 4:
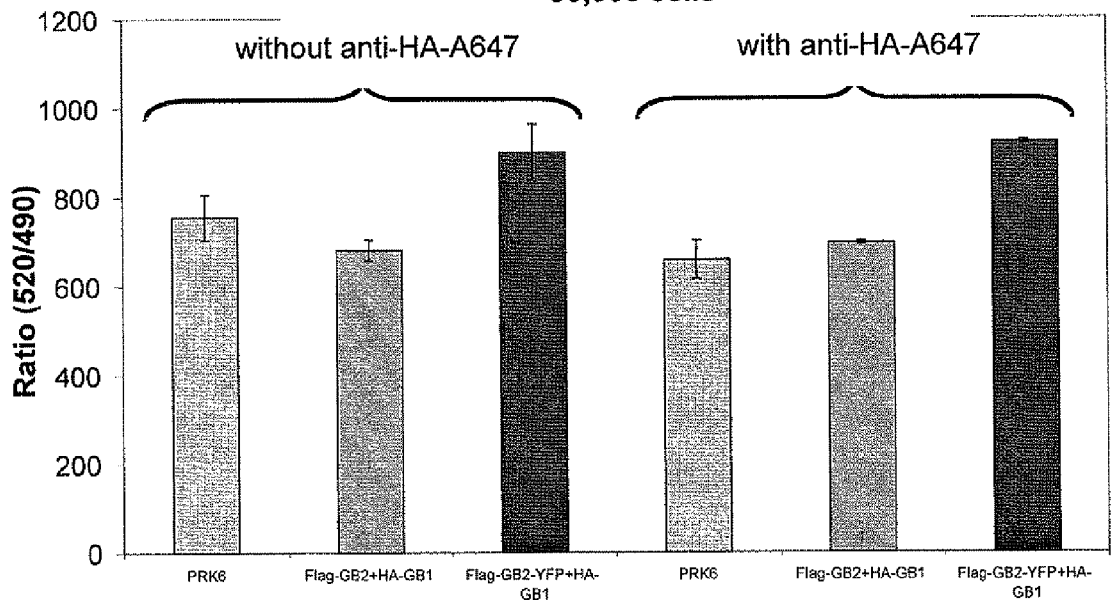
FIG. 4 shows ratio of the luminescence of the acceptor compound (YFP, measured at 520 nm) against that of the donor compound (terbium cryptate, measured at 490 nm), in various experimental conditions. This figure confirms the existence of transmembrane FRET.

The results presented in FIG. 4 show an increase in the observed ratio with the dimer GB 1/GB2 in the presence of terbium and YFP, corresponding to a delta F value of between 37 and 40%.

This experiment shows for the first time the existence of a transmembrane TR-FRET between terbium cryptate located on the outer face of the plasma membrane and YFP located on the inner face of this membrane.

Similar results are obtained for wells containing 100,000 cells or when the terbium cryptate is replaced with a europium cryptate.

LIST OF DOCUMENTS CITED IN THE DESCRIPTION

1. D. Maurel et al., Analytical Biochemistry 329 (2004), 253-262: "Cell surface detection of membrane protein interaction with homogeneous time-resolved fluorescence resonance energy transfer technology."
2. J. P. Pin et al., Biochemical Pharmacology 68 (2004), 1565-1572: "Activation mechanism of the heterodimeric $GABA_B$ receptor."
3. J. Liu et al., The Journal of Biological Chemistry, vol. 279 (2004), n° 16, 15824-15830: "Molecular Determinants Involved in the Allosteric Control of Agonist Affinity in the $GABA_B$ Receptor by the $GABA_{B2}$ Subunit."
4. Tsien et al., (1997), U.S. Pat. No. 5,661,035.
5. Gonzalez et al., Chemistry and Biology, (1997), 4, 269-277: "Improved fluorescent indicators of cell membrane potential that use fluorescence resonance energy transfer."
6. Gonzalez et al., DDT, (1999), 4, 9, 431-439: "Cell-based assays and instrumentation for screening ion-channel targets."
7. Chollet et al., J. of Computer-Aided Molecular Design, (1999), 13, 209-219; "Biophysical approaches to G protein-coupled receptors: structure, function and dynamics."
8. Turcatti et al., J. Biological Chemistry, (1996), 271, 33, 19991-19998: "Probing the structure and function of the Tachykinin Neurokinin-2 Receptor through biosynthetic incorporation of fluorescent amino acid at specific sites."
9. Chan et al., Cytometry, (2001), 44, 361-368: "Fluorescence resonance energy transfer analysis of cell surface receptor interactions and signaling using spectral variants of the green fluorescent protein."
10. Wilson et al., J. Biological Chemistry, (2002), 277, 5, 3666-3672: "Fluorescence resonance energy transfer study on the interaction between the lactate transporter MCT1 and CD147 provide information on the topology and stoichiometry of the complex in situ."
11. Guignet et al., Nature Biotechnology, (2004), 4, 440-444: "Reversible site-selective labeling of membrane proteins in live cells."

The invention claimed is:

1. A method of revealing a biological process using a FRET measurement, comprising
incorporating, into a measurement medium containing a plasma membrane, a biological entity X coupled with a first member of a pair of FRET partners and a second biological entity Y coupled with the second member of the pair of FRET partners, wherein
the biological entities are each, independently from one another, an intrinsic or an extrinsic membrane protein, a transmembrane protein, a cytosoluble compound, a test ligand or an antibody, and
the energy-donating member of the pair of FRET partners is a rare earth chelate or a rare earth cryptate, and the acceptor fluorophore is a rhodamine, a cyanin, a squaraine, a difluoroboradiazaindacene (BODIPY), a fluorescein, a compound of the ALEXFLUOR family of compounds, a quantum dot, a phycobiliprotein, a GFP or a derivative thereof which is YFP or CFP, or a fluorescent coral protein, the members of said pair of FRET partners being located on either side of the plasma membrane;
exciting the measurement medium at the excitation wavelength of the energy-donating member; and
measuring the FRET signal or the variations in said signal emitted in said culture medium.

2. The method according to claim 1, further comprising stimulating the measurement medium via chemical, thermal, electrical or mechanical stimulation.

3. The method according to claim 2, wherein the stimulation is a chemical stimulation and the method further comprises adding a chemical test compound to the measurement medium, and measuring the FRET signal in the presence and absence of the test compound.

4. The method according to claim 3, wherein the biological process is a conformational change of a transmembrane receptor, wherein the biological entities X and Y are one and the same transmembrane receptor labeled on either side of the membrane with a donor fluorescent compound and an acceptor fluorescent compound, and wherein the test compound is a compound capable of binding to said transmembrane receptor, wherein a variation in the FRET signal is indicative of a modification of the conformation of said receptor in the presence of said test compound.

5. The method according to claim 1, wherein the biological entities X and Y are transmembrane proteins and wherein the biological process is a variation in the interaction between these two proteins, wherein a variation in the FRET signal is indicative of a variation in interaction between said proteins.

6. The method according to claim 5, wherein said transmembrane proteins X and Y are identical proteins, one of them being labeled with a donor fluorescent compound and the other with an acceptor fluorescent compound, the donor and acceptor fluorescent compounds being located on either side of said membrane, wherein the variation in the FRET signal is indicative of a homodimerization phenomenon.

7. The method according to claim 6, wherein the measured interaction is the homodimerization of a $GABA_B$ receptor.

8. The method according to claim 5, wherein the measured interaction is a heterodimerization.

9. The method according to claim 5, wherein a test ligand capable of affecting the dimerization of said transmembrane proteins is added to the measurement medium, and wherein the FRET signal is measured in the presence and absence of said test ligand.

10. The method according to claim 1, wherein the biological entity X is a cytosoluble compound and in that the biological entity Y is an intrinsic or extrinsic membrane protein, wherein the variation in the FRET signal is indicative of a phenomenon of translocation of said cytosoluble compound to or from said membrane protein.

11. The method according to claim 10, wherein a test compound capable of affecting the translocation of said cytosoluble compound to or from said membrane protein is added to the measurement medium, and wherein the FRET signal is measured in the presence and absence of said test compound.

12. The method according to claim 10, wherein the membrane protein is a transmembrane receptor and wherein the cytosoluble compound is arrestin or a G protein.

13. The method according to claim 1, wherein the biological entity X is a transmembrane receptor located on the plasma membrane and labeled in its intracellular part with a member of a pair of donor/acceptor fluorescent compounds, and the biological entity Y is a potential ligand for said transmembrane receptor which forms part of a bank of test compounds and is labeled with the other member of the pair of donor/acceptor fluorescent compounds, wherein the variation in the FRET signal in the presence or absence of said compound Y is indicative of the binding of Y to said transmembrane receptor.

14. The method according to claim 1, wherein the biological entity X is a transmembrane receptor located on the plasma membrane and labeled in its intracellular part with a member of a pair of donor/acceptor fluorescent compounds, and the biological entity Y is a known ligand for said transmembrane receptor which is labeled with the other member of the pair of donor/acceptor fluorescent compounds, and wherein a test compound is added to the measurement medium, the variation in the FRET signal in the presence or absence of said test compound being indicative of the binding of said test compound to said transmembrane receptor X.

15. The method according to claim 1, wherein the fluorophore compound has a lifetime of between 100 ns and 5000 µs.

16. The method according to claim 15, wherein the fluorophore is europium or terbium.

17. The method according to claim 16, wherein the fluorophore is a rare earth cryptate containing a pyridine unit.

18. The method according to claim 17, wherein the fluorophore is a terbium cryptate and the acceptor fluorescent compound is a fluorescent protein.

19. The method according to claim 1, wherein the
coupling of the biological entity X or Y with the donor and acceptor fluorescent compounds comprises coupling by covalent bonding;
indirect coupling by a biotin/streptavidin system or a tag/anti-tag antibody system which is a 6HIS/anti-6HIS system, a FLAG/anti-FLAG system, a DNP/anti-DNP system, a GST/anti-GST system, a c-myc/anti-c-myc system or a HA/anti-HA system; or
coupling via an antibody specific for the entity X or Y to be labeled.

20. The method according to claim 1, wherein the phycobiliprotein is B-phycoerythrin, R-phycoerythrin, or C-phycocyanin.

21. The method according to claim 1, wherein the fluorophore compound has a lifetime of between 100 and 3000 µs.

22. The method according to claim 1, wherein the coupling of the biological entity X or Y with the donor and acceptor fluorescent compound is effected by expressing a fusion protein between said biological entities X or Y and a protein with irreversible enzymatic activity, which transfers the fluorophore onto said biological entity X or Y.

23. The method according to claim 22, wherein protein with irreversible enzymatic activity is an $O^6$-alkylgunaine DNA-alkyltransferase or a dehalogenase.

* * * * *